US009377521B2

(12) United States Patent
Li et al.

(10) Patent No.: US 9,377,521 B2
(45) Date of Patent: *Jun. 28, 2016

(54) HYGIENE MONITORING AND MANAGEMENT SYSTEM AND METHOD

(71) Applicant: Diversey, Inc., Sturtevant, WI (US)

(72) Inventors: Anderson Chung Kong Li, Nottingham (GB); Anup Bhagvanji, Nottingham (GB)

(73) Assignee: Diversey, Inc., Sturtevant, WI (US)

( * ) Notice: Subject to any disclaimer, the term of this patent is extended or adjusted under 35 U.S.C. 154(b) by 31 days.

This patent is subject to a terminal disclaimer.

(21) Appl. No.: 14/338,022

(22) Filed: Jul. 22, 2014

(65) Prior Publication Data

US 2014/0333433 A1  Nov. 13, 2014

Related U.S. Application Data

(63) Continuation of application No. 13/254,093, filed as application No. PCT/US2010/025936 on Mar. 2, 2010, now Pat. No. 8,786,429.

(60) Provisional application No. 61/156,569, filed on Mar. 2, 2009.

(51) Int. Cl.
| G08B 23/00 | (2006.01) |
| G01S 5/02 | (2010.01) |
| G01S 11/06 | (2006.01) |
| G06Q 10/06 | (2012.01) |
| G01S 11/02 | (2010.01) |
| G01S 13/46 | (2006.01) |

(52) U.S. Cl.
CPC . *G01S 5/02* (2013.01); *G01S 11/02* (2013.01); *G01S 11/06* (2013.01); *G06Q 10/06* (2013.01); *G01S 2013/466* (2013.01)

(58) Field of Classification Search
CPC ....................................................... G06Q 10/08
USPC ........ 15/501; 205/687; 235/375; 340/539.13, 340/573.1, 8.1; 422/5; 700/245, 253, 262; 701/2, 23, 300
See application file for complete search history.

(56) References Cited

U.S. PATENT DOCUMENTS

| 6,727,818 | B1 * | 4/2004 | Wildman et al. | 340/573.1 |
| 6,975,231 | B2 * | 12/2005 | Lane et al. | 340/573.1 |
| 7,242,307 | B1 * | 7/2007 | LeBlond et al. | 340/573.1 |
| 7,323,991 | B1 * | 1/2008 | Eckert et al. | 340/572.1 |
| 7,706,917 | B1 * | 4/2010 | Chiappetta et al. | 700/245 |
| 7,737,861 | B2 * | 6/2010 | Lea et al. | 340/8.1 |
| 8,400,268 | B1 * | 3/2013 | Malik et al. | 340/8.1 |
| 8,400,309 | B2 * | 3/2013 | Glenn et al. | 340/573.1 |

(Continued)

*Primary Examiner* — Benjamin C Lee
*Assistant Examiner* — Israel Daramola
(74) *Attorney, Agent, or Firm* — Michael Best & Friedrich, LLP

(57) ABSTRACT

A Real Time Locating System (RTLS) hygiene management and monitoring system for individuals and companies to manage and monitor the hygiene of their surroundings. In some embodiments of the invention, RTLS is used to monitor and manage cleanliness of rooms and surfaces and the location of cleaning supplies and cleaning personnel. The invention provides improved efficiency and quality of hygiene services. For instance, the invention can enable prioritization of cleaning, improve efficient use of cleaning supplies and cleaning personnel, track short and long term cleaning operations, and provide insight into ineffective cleaning.

21 Claims, 13 Drawing Sheets

(56) References Cited

U.S. PATENT DOCUMENTS

| | | | |
|---|---|---|---|
| 8,405,503 B2* | 3/2013 | Wong | 340/539.13 |
| 2002/0120364 A1* | 8/2002 | Colens | 700/262 |
| 2005/0035862 A1* | 2/2005 | Wildman et al. | 340/573.1 |
| 2005/0171644 A1* | 8/2005 | Tani | 700/253 |
| 2005/0192707 A1* | 9/2005 | Park et al. | 700/259 |
| 2006/0132316 A1* | 6/2006 | Wildman et al. | 340/573.1 |
| 2007/0016328 A1* | 1/2007 | Ziegler et al. | 700/245 |
| 2007/0244610 A1* | 10/2007 | Ozick et al. | 701/23 |
| 2008/0206092 A1* | 8/2008 | Crapser et al. | 422/5 |
| 2008/0273791 A1* | 11/2008 | Lee et al. | 382/153 |
| 2009/0212103 A1* | 8/2009 | Li et al. | 235/375 |
| 2009/0216449 A1* | 8/2009 | Erko et al. | 701/300 |
| 2010/0134296 A1* | 6/2010 | Hwang | 340/573.1 |
| 2010/0147700 A1* | 6/2010 | Field et al. | 205/687 |
| 2011/0273298 A1* | 11/2011 | Snodgrass et al. | 340/573.1 |
| 2012/0036659 A1* | 2/2012 | Ziegler et al. | 15/50.1 |
| 2013/0204463 A1* | 8/2013 | Chiappetta | 701/2 |

* cited by examiner

HYGIENE MONITORING AND MANAGEMENT SYSTEM AND METHOD

CROSS-REFERENCE TO RELATED APPLICATIONS

This application is a continuation of U.S. patent application Ser. No. 13/254,093, filed Aug. 31, 2011, which is a national phase application filing of International Patent Application No. PCT/US2010/025936, filed Mar. 2, 2010, which claims the benefit of and priority to U.S. Provisional Application No. 61/156,569, filed on Mar. 2, 2009, the entire contents of each of which are incorporated herein by reference.

BACKGROUND

The present invention relates to systems and methods of monitoring and managing hygiene using a real-time locating system (RTLS).

SUMMARY

By using RTLS, individuals and companies can monitor and manage the hygiene of their surroundings. In some embodiments of the invention, RTLS is used to monitor and manage cleanliness of rooms and surfaces and the location of cleaning supplies and cleaning personnel. Embodiments of the invention provide improved efficiency and quality of hygiene services. For instance, embodiments can enable prioritization of cleaning, improve efficient use of cleaning supplies and cleaning personnel, track short and long term cleaning operations, and provide insight into ineffective cleaning.

Embodiments of the invention include a hygiene monitoring and management system. The system includes a wireless tag and a monitoring module. The wireless tag is operable to transmit distance signals, wherein each distance signal indicates a tag distance between the wireless tag and an associated access point and wherein the tag distance is based on a strength of a wireless signal from the associated access point received by the tag. The monitoring module is operable to track movement of the wireless tag by repeatedly determining the location of the wireless tag based on the tag distances. The monitoring module is also operable to determine a cleanliness level of an area based on tracking movement of the wireless tag.

Some embodiments of the invention include a display unit, wherein the monitoring module is operable to graphically depict the determined cleanliness level of the area and the location of the wireless tag on the display unit. In some embodiments, the determination is based on at least one of a clean signal and a dirty signal received from a fixed call actuator in the area or coupled to a wall bounding the area. Some embodiments of the invention further include a cleaning implement including a wireless tag, wherein the monitoring module is operable to indicate the cleanliness level of the area based on the tracked movement of the cleaning implement.

Another embodiment of the invention includes a method of hygiene monitoring and management. The method includes receiving, by a wireless tag, wireless signals from a plurality of access points and receiving, by each access point, an associated tag distance from the wireless tag. Each associated tag distance represents a strength of each associated access point's wireless signal at the wireless tag. The method further includes repeatedly determining a location of the wireless tag based on the tag distances to track movement of the wireless tag. The method also includes determining a cleanliness level of an area based on tracking the movement of the wireless tag.

In some embodiments, the method further includes graphically displaying a floor plan with a plurality of areas including the area, a cleanliness level of each of the plurality of areas, and at least one of a current location of the wireless tag on the floor plan and a path indicating the tracked movement of the wireless tag on the floor plan.

In some embodiments, the wireless tag is secured to a spray device and a second wireless tag is secured to a wiping device. The monitoring module determines a surface cleanliness level of a surface within the area based on: 1) predicting a spray pattern of the spray device on the surface based on tracking the movement of the spray device and detecting a dispensement by the spray device, and 2) estimating an effective wipe area on the surface based on the spray pattern and tracking movement of the wiping device.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Embodiments of the invention determine the position of a tagged item relative to access points that are generally fixed. This determination is sometimes described as triangulation or trilateration, and includes the ability to approximately measure the distance between an access point and a wireless device using a Relative Signal Strength Indicator (RSSI). Generally, the stronger a signal, the higher the RSSI level, and the nearer a wireless device is to an access point measuring the RSSI. In place of or in combination with a RSSI measurement, other measurement techniques can be used, such as a Received Channel Power Indicator (RCPI). For convenience and simplification, examples involving RSSI will be used throughout the disclosure.

Figure 1:
FIGS. 1-3 show fixed points used to determine a mobile device location.
Figure 2:
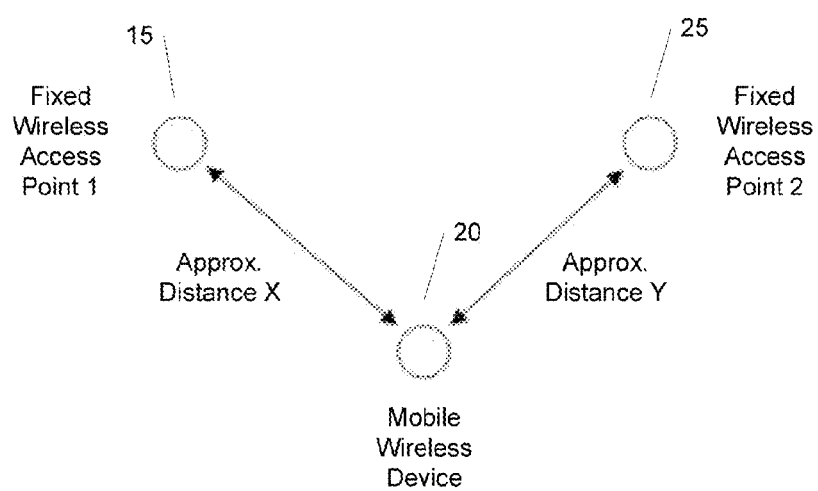
Figure 3:
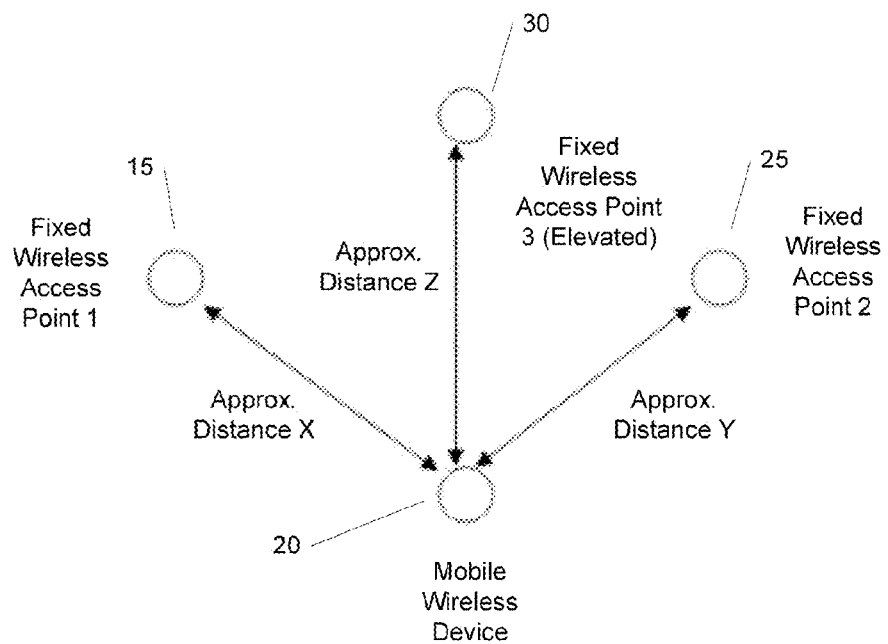

FIGS. 1-3 depict how fixed access points can be used to determine the position of a mobile wireless device. FIG. 1 includes a fixed access point 15 and a mobile wireless device 20. The fixed wireless access point 15 has the ability to measure the approximate distance x between the two points by measuring the RSSI. If the location of the fixed access point 15 is known, then the location of the mobile wireless device 20 is known to be at a radius of x from the fixed access point. With only one measurement x from the fixed access point 15, one cannot determine the direction of the mobile wireless device 20 relative to the fixed access point 15. The location of mobile wireless device 20 can be imagined as at some point on the surface of a sphere of radius x surrounding the fixed wireless access point 15.

In FIG. 2, a second fixed wireless access point 25 is introduced to the system including fixed wireless access point 15 and mobile wireless device 20. The fixed wireless access point 25 can measure the RSSI of the mobile wireless device 20 to determine that the mobile wireless device 20 is an approximate distance y from the fixed access point 25. If the location of the fixed access point 25 is known, then the location of the mobile wireless device 20 is known to be at a radius of y from the fixed access point 25. In addition, the location of the mobile wireless device 20 is still known to be at a radius of x. Therefore, the possible locations can be narrowed down to the intersection points of a first sphere (having its center at fixed wireless access point 15 and radius x) and a second sphere (having its center at fixed wireless access point 25 and radius y). The intersection points of these two spheres will either form a single point or form a circle on the y-z plane (the fixed wireless access points are on the x-y plane).

In FIG. 3, a third fixed wireless access point 30 is introduced to the system including mobile wireless device 20 and fixed wireless access points 15 and 25. The fixed wireless access point 30 can measure the RSSI of the mobile wireless device 20 to determine that the location of the mobile wireless device 20 is at a radius of z from the fixed access point 30. This location information can be combined with the knowledge that the mobile wireless device 20 is also a radius x from fixed wireless access point 15 and y from fixed wireless device 14 (which as described above, requires the mobile wireless device 20 to be at the intersection of two spheres). The intersection of the third sphere (having fixed wireless access point 30 as its center and radius z) with the first and second spheres described above gives the possible locations of the mobile wireless device 20. The possible locations will be either at a single point or at two intersection points on the circle on the y-z plane formed by the intersection of the three spheres.

Determining a fourth distance between a fourth fixed wireless access point (not shown) and a mobile wireless device 20 or using other information (e.g., knowing that one of the potential location points resides outside of an acceptable area for the mobile wireless device 20) can be used to select the proper intersection point of the three spheres as the true location of the mobile wireless device. With additional known data about a particular mobile wireless device, other fixed wireless access points can be unnecessary to determine location. For instance, if it is known that a floor cleaner will be 1) in a particular room and 2) on the floor during operation, these two pieces of information can be used with two RSSI measurements from fixed wireless access points to pinpoint the mobile wireless device's location.

The triangulation techniques described above can be used to form a RTLS hygiene management and monitoring system on a WLAN network using Wi-Fi based Radio Frequency Identification (RFID) mobile wireless devices (i.e., tags). The hygiene management and monitoring system can monitor and manage multiple tags, which can be placed on objects or personnel. Wi-Fi based RTLS technology can accurately locate devices within 1 meter and less. The accuracy can be improved by increasing the number of access points installed and by improving signal strength measuring technology. Alternative RTLS wireless technologies can include Ultra-Wide Band (UWB), Ultrasound technology, and global positioning satellites (GPS) for locating objects; any wireless technology suitable for RTLS is also within the scope of this disclosure.

Figure 4:
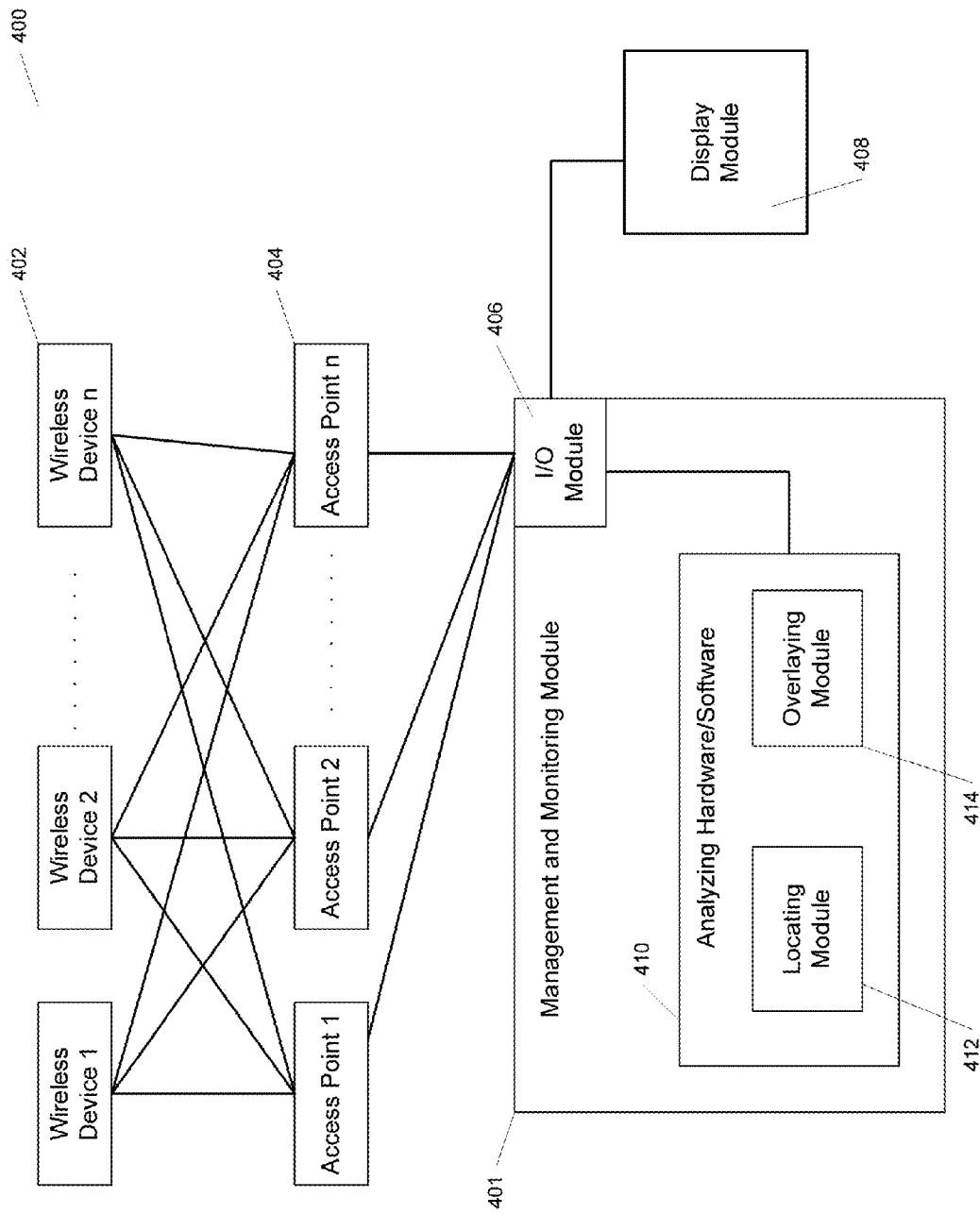
FIG. 4 shows exemplary components of a RTLS hygiene management and monitoring system.

FIG. 4 depicts components of one exemplary embodiment of a hygiene management and monitoring system 400. Wireless devices 402 are the mobile items to be located or tracked using RTLS. The wireless devices 402 receive a signal from the access points 404 in wireless range and determine the strength of the signal. In turn, the wireless devices 402 output a distance signal. In some embodiments, the wireless devices 402 calculate the distance from the access point associated with a received signal and output a distance signal as an actual distance value (e.g., 5 meters). In other embodiments, the wireless devices 402 output a distance signal as a strength value that is used to calculate a distance value. For instance, a strength signal of 60 out of a possible 100 may represent 5 meters. By these techniques, the access points 404 can be used to measure the RSSI of the wireless devices 402 within range. The I/O module 406 of the management and monitoring module 401 receives the measured RSSI. The measured RSSI data is sent to the analyzing hardware/software 410 to calculate the estimated distance from the wireless device 402 or, if the access points 404 performed the distance calculations, the I/O module 406 receives and forwards the estimated distance from the wireless device 402.

The analyzing hardware/software 410 can include hardware components, software components, or a combination thereof, and receives the data input through the I/O module 406. The locating module 412 receives multiple RSSI or distance measurements for a given wireless device 402 and uses the procedures described in FIGS. 1-3 to determine a location of the wireless device. Alternatively, the measurements can be matched to a database of stored values related to the various possible locations in an area to be monitored. Thereafter, the overlaying module 414 can plot or assign a value representing the location of the wireless device 402 on a previously stored map of the area where the hygiene managing and monitoring is occurring. The plotted locations or location values of the wireless devices 402 and the previously stored map can then be output through the I/O module and sent to a display module 408 as a graphical display for a user of the hygiene management and monitoring system. Alternatively, the data can be sent to a computer or storage device either directly or indirectly through a local or wide area network, the Internet, or the like.

Figure 5:
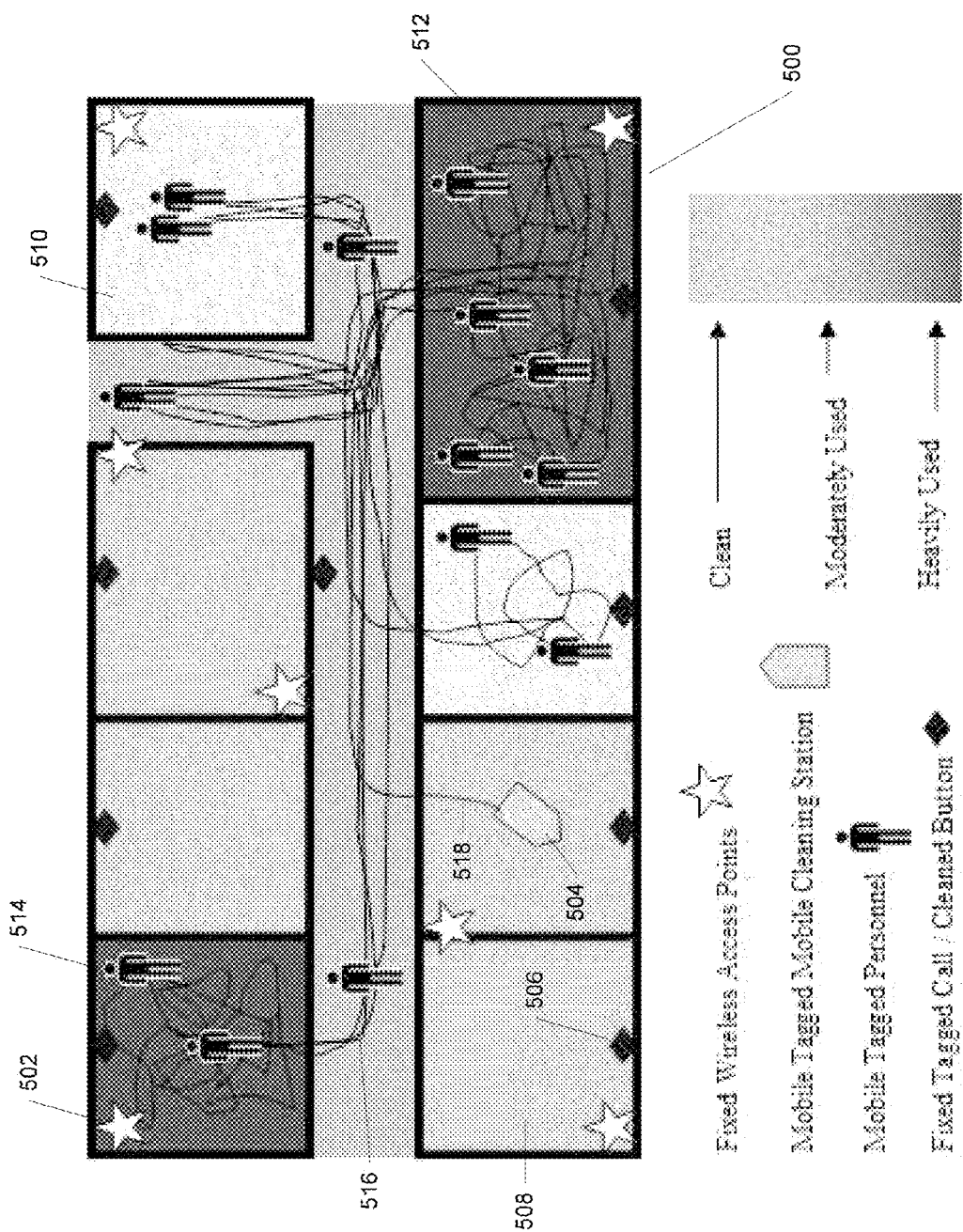
FIG. 5 shows a graphical display of RTLS room cleanliness monitoring.

Although multiple methods can be used to set up RTLS at various locations, one exemplary arrangement of a RTLS in an existing building is depicted in FIG. 5. One exemplary arrangement method for this RTLS can be generally broken down into three categories: installation, calibration, and operation.

Two steps are performed during installation: 1) providing an adequate wireless network and 2) installing the RTLS engine. To provide an adequate wireless network, a survey of the existing network infrastructure can be performed. From the survey, a determination can be made regarding whether the existing wireless network can be used or updated, or if a new wireless network must be installed. Some factors used to determine the ability of the existing network include the number of wireless access points, the wireless network coverage of a location, and the speed at which the network can retrieve information. The more wireless access points in the network and the greater the speed of the network, the more accurately, reliably, and quickly a wireless device's location can be identified.

In the second step, the RTLS engine, which may be software based, is installed to be run by the backbone system residing on the network. For instance, the RTLS engine can be installed as a service on an existing computer server as part of the network infrastructure. The RTLS engine can be programmed to recognize specific mobile wireless devices (also known as tags), either by each tag's identification code or by other detectable features of the tag. The performance requirement of the computer server to run the RTLS engine is proportional to the number of wireless devices and accuracy requirements. If the existing computer server provides inadequate performance, a standalone RTLS system can be installed on the network. In addition, the backbone system can be extended to be run offsite if the wireless technology, network speed, and security permit. The backbone system can reside anywhere on a PAN, LAN, WLAN, WAN, or MAN to suit the application need.

In other embodiments, the location determining functions of the RTLS engine can be included in the wireless device itself. The wireless device can then calculate its own positional coordinates relative to the measured signal strength of fixed devices using, for example, one of the location determining methods described herein. The coordinates can then be sent to a main RTLS engine for further processing. The main RTLS engine can perform the same functions as other RTLS engines, either excluding or duplicating those functions outsourced to the wireless devices.

To calibrate the system, a predicted signal strength map of the location is produced. This map can be used for determining tag location and is overlaid on a floor plan of the location where RTLS is to be implemented. The predicted signal strength map can be created using estimated signal strength calculations based on wireless access point locations and characteristics. For greater accuracy, CAD designs including building materials are used to better predict signal strength at different points in the building. To complete the calibration, a physical survey can be performed to measure the actual signal strengths of a tag at different locations and compare and update the predicted signal strength map for better accuracy. The predicted signal strength map can be stored as a database. The database can contain RSSI values and their associated fixed access points as index values that reference the stored predicted location values.

Finally, operation of the RTLS includes the wireless access points receiving tag broadcasts and using location algorithms to determine the tag's location. The wireless access points can measure the signal strength and determine the source of the received tag broadcasts and relay the information to the RTLS engine. In some instances, the RTLS engine sends a request signal to the wireless access points, at which point, the wireless access points will provide the signal strength and tag identifying information to the RTLS engine. The RTLS engine can then use the measured signal strengths and tag identifying information as indexes to reference a location on the floor plan using the predicted signal strength map database.

Alternatively, the measured signal strengths and tag identifying information can be used to determine the tag location as described with reference to FIGS. 1-3. In another embodiment, the RTLS engine may determine tag locations through a logged history of last known tag locations. This approach reduces the need to broadcast across the entire wireless network, thus reducing the load on the network each time a tag is to be located. In yet another embodiment, the RTLS engine may receive tag identifying information and tag location coordinates directly from the wireless devices that are adapted to perform their own location determining functions. In some embodiments, the RTLS engine can use determined tag locations over time to plot the tag's movement on the floor plan. The more frequent the received tag broadcasts, the more accurately the RTLS engine can plot the tag's movement.

Tags can operate in two modes to communicate with the RTLS engine: 1) in a passive mode, where a tag remains in a sleeping state until receipt of a wake-up signal, upon which the device broadcasts, and 2) in an active mode, where a tag automatically broadcasts at selected time intervals without requiring receipt of a wake-up signal. For example, if a tag is to be continuously tracked and monitored, an active mode may be chosen. Conversely, if a tag is only to be located intermittently, a passive mode may be chosen. A combination of active and passive modes may also be used by a tag.

Three exemplary implementations of a RTLS to be used for a hygiene monitoring and management system include 1) a room cleanliness monitoring system, 2) a surface area monitoring system, and 3) a three-dimensional surface management and monitoring system.

The first implementation is a room cleanliness monitoring system using a RTLS and will be described with reference to FIGS. 5 and 6. FIG. 5 shows a graphical layout 500 of a floor of a building where room cleanliness will be monitored. Fixed wireless access points 502 are positioned around a building as described above and shown in FIG. 5. Mobile tagged personnel, such as a cleaning worker 514, carry or have attached active wireless tags (not shown). The active tags continuously or periodically broadcast signals that the fixed wireless access points 502 receive. A room cleanliness monitoring system determines and records the location of these active tags by using signal strengths of the active tags as described above. The room cleanliness monitoring system can use the recorded active tag locations to plot paths 516 over the graphical layout 500.

The room cleanliness monitoring system can also display the room cleanliness by way of a color-coded system. For instance, FIG. 5 uses a color-coded key such that the darker the room, the more heavily used and dirtier the room. Room 512 is an example of a more heavily used room, room 510 is clean, and room 508 has an intermediate level of use. Additionally, each room and hallway can include a call/cleaned button 506 that is in a fixed position and includes a tag. The button 506 can be a passive device that is activated by personnel to indicate that a room needs to be cleaned or that it has been cleaned. In response, the room cleanliness monitoring system can update the room color displayed. In some embodiments, multiple buttons can be provided.

Also shown in FIG. 5 is mobile tagged cleaning station 504, which can transmit information to fixed wireless access points 502 relating to, for example, cleaning materials, equipment, chemicals, and other items associated with a cleaning station. The mobile tagged cleaning station 504 can also have a response button or device (not shown) that can be triggered by an operator to indicate that a room has been cleaned. The fixed wireless access points 502 can also receive broadcasts from the mobile tagged cleaning station 504 and, in turn, the room cleanliness monitoring system can determine and record the location of the cleaning station 504 by using the fixed wireless access points. The room cleanliness monitoring system can use the determined cleaning station 504 locations to plot path 518 over the graphical layout 500.

One exemplary method of operating the room cleanliness monitoring system of FIG. 5 will next be described with reference to FIG. 6. In a first step 600, the room cleanliness monitoring system will determine if a room needs to be cleaned based on the room cleanliness data displayed as color-coded rooms in FIG. 5. The system can prioritize based on the type of room, the level of dirtiness, and the room's location relative to cleaning personnel, supplies, and mobile cleaning stations. If a room is at a level such that it needs to be cleaned, the room cleanliness monitoring system will locate the best-suited mobile cleaning station 504 in step 602. The determination of the best-suited mobile cleaning station 504 can consider a mobile cleaning station's proximity to the room to be cleaned, its current availability, its available cleaning supplies, and its available cleaning equipment. For instance, the nearest mobile cleaning station 504 that is not currently cleaning another room, and contains the necessary cleaning supplies and equipment for the job, would be selected.

Upon determining the best-suited mobile cleaning station 504, the room cleanliness monitoring system will send a call signal to the mobile cleaning station 504 in step 604. Thereafter, in step 605 the room cleanliness monitoring system checks if a room cleaned signal has been received either by a dispatched mobile cleaning station 504 or a call/cleaned button 506. Step 605 is also performed if it is determined that no room needs to be cleaned in step 600. In step 606, after a room cleaned signal has been received, the room cleanliness monitoring system updates the graphical layout 500 to show that the room is clean. The room cleanliness monitoring system can then restart the process in step 600.

Multiple mobile cleaning stations, rooms, personnel, and hallways can be tracked to allow for multiple dispatches and efficient scheduling of cleaning. Moreover, the room usage and cleanliness and tag location and tracking can be periodically reviewed and analyzed by employees, employers, software and/or auditors to identify and eliminate inefficiencies in hygiene management.

Figure 7:
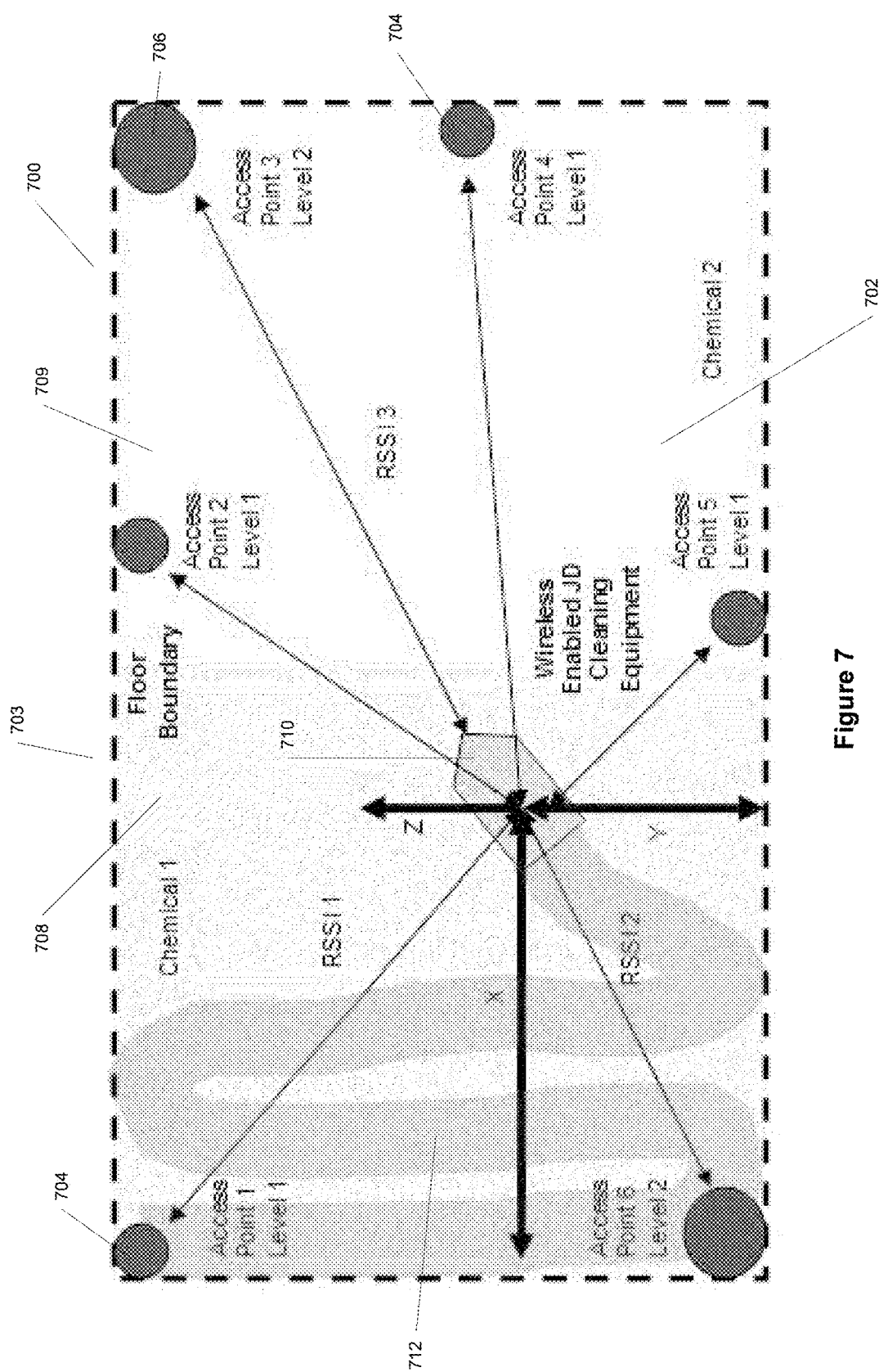
FIG. 7 shows a graphical display of RTLS surface area monitoring.

A second implementation is a surface area monitoring system using a RTLS and will be described with reference to FIGS. 7 and 8. FIG. 7 shows a graphical layout 700 of a floor 702 of a room 703 to be cleaned. Several level 1 access points 704 and level 2 access points 706 are distributed within the outside boundaries of a room (shown by the dotted line), but at different levels.

In one embodiment, an active RFID device (not shown) is placed on a floor cleaning device 710. The floor cleaning device 710 can hold different chemicals, and the chemicals may be held at different dilution levels. The floor cleaning device 710 may also be configured to dispense different chemicals and alter the dilution levels during a cleaning process. Using RTLS as described above, the location of the floor cleaning device 710 may be tracked and plotted on the graphical layout 700 as a path 712. The floor cleaning device 710 may begin to be tracked automatically upon start up or by manual enabling.

As the floor cleaning device 710 moves from area to area, the chemical and dosing dilution can be adjusted wirelessly by the intelligent cleaning system to suit the mapped zones. For instance, the type of chemicals and dilution levels can be adjusted according to what types of rooms are being cleaned, how often the rooms are cleaned, how often the rooms are used, and/or how dirty the floors are determined to be. If a zone is cleaned infrequently or is heavily used, a stronger chemical or higher concentration can be used. The stronger chemical or higher concentration can clean the room better initially and keep the room cleaner for longer periods of time. If a zone is cleaned more often and is infrequently used, a lower concentration may be more desirable to reduce the amount of chemicals used. Reducing the amount of chemicals to create a more efficient floor cleaning device 710 has various benefits, including reduction of waste, reduction of cost, and reduction of time spent refilling the floor cleaning device 710 with new chemicals.

Figure 6:
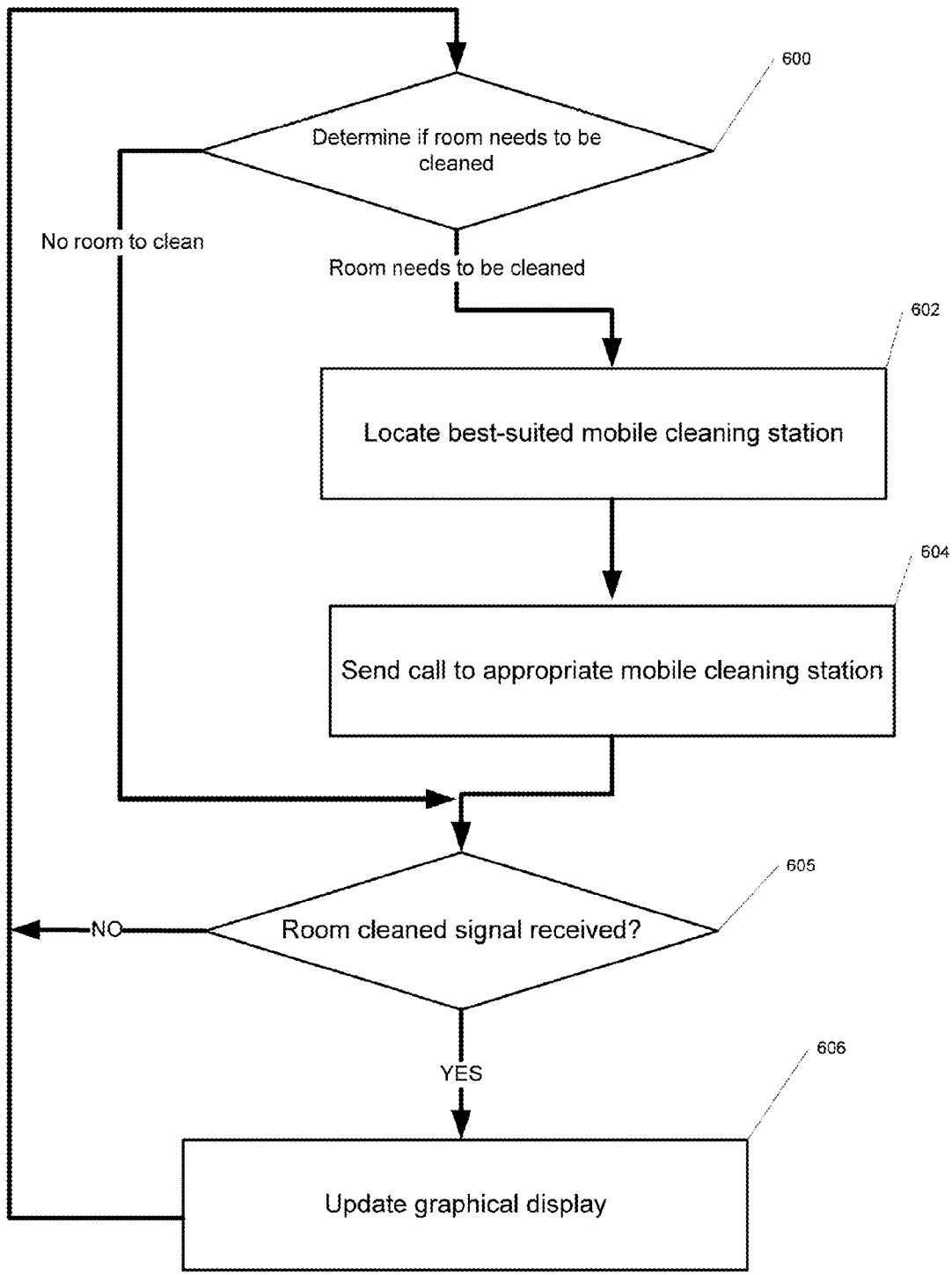
FIG. 6 shows a method of room cleanliness monitoring using RTLS.

For example, in FIG. 7, the left half of the floor is determined to be dirtier based on its heavier use as tracked with a room cleanliness monitoring system described in FIGS. 5 and 6. In turn, chemical 1, a strong or highly concentrated chemical, is used on the left half of the floor 708, but chemical 2, a weaker or less concentrated chemical, is used on the right half of the floor 709.

Using the RTLS surface area monitoring system to plot the timing and movement of the floor cleaning device 710 when in use can provide additional benefits and uses. For instance, the paths plotted can be reviewed for reporting purposes or for determining whether the room must be cleaned again. The paths plotted can be stored to build an intelligent picture using gradients of colors to represent the cleaning behavior over time. This data can be used to further influence more efficient and better practices by identifying surfaces that are missed regularly and those that are over-cleaned.

Figure 8:
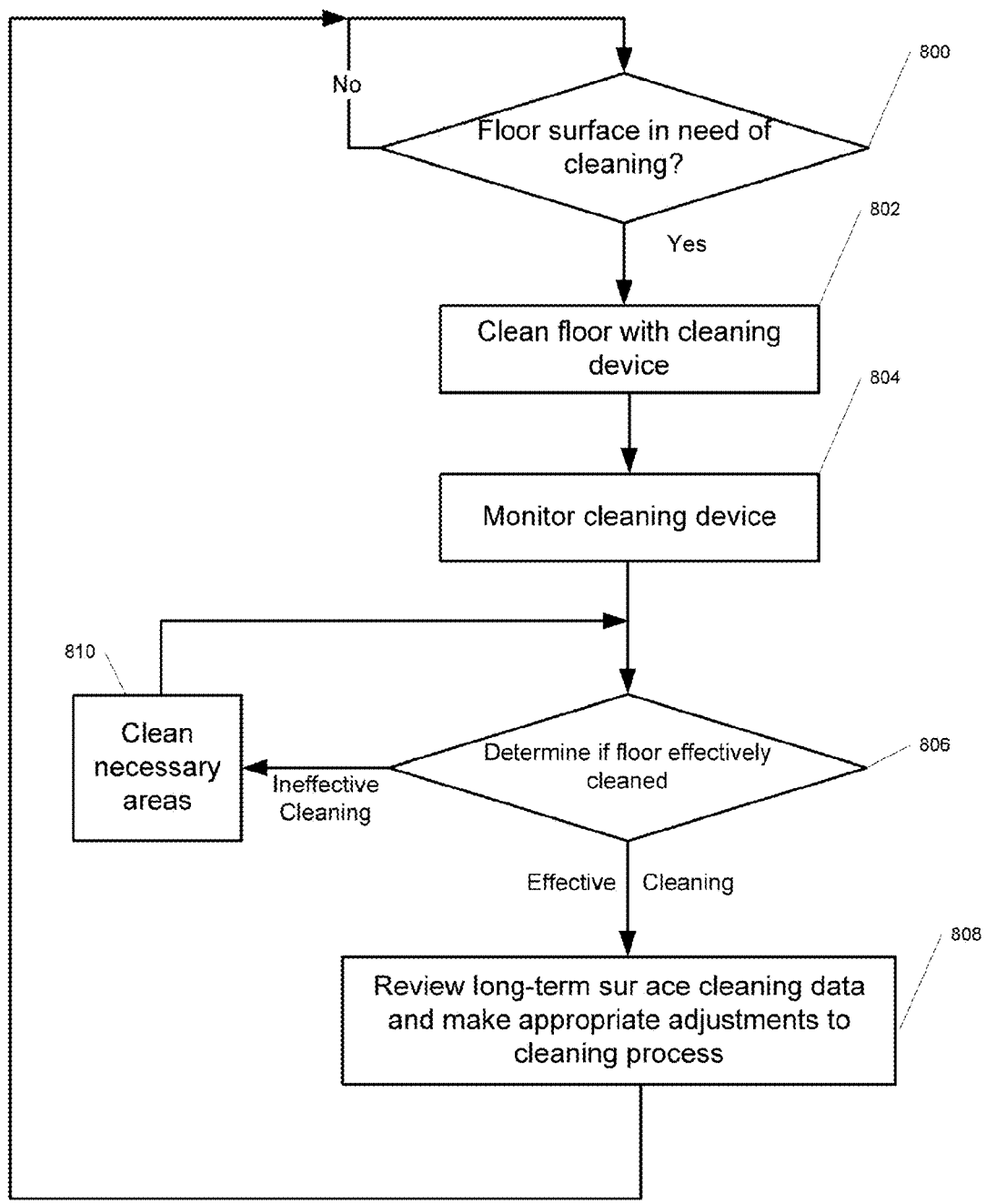
FIG. 8 shows a method of surface area monitoring using RTLS.

FIG. 8 shows a flow chart for an exemplary method of operating the surface area monitoring system of FIG. 7. In step 800, a worker or the surface area monitoring system determines whether a surface area needs to be cleaned. If a surface area (such as floor 709) is determined to be in need of cleaning, a worker will clean the floor using a floor cleaning device 710 in step 802. In step 804, the surface area monitoring system will monitor the cleaning of the floor surface area by tracking the location of the floor cleaning device 710 and the disbursement of chemicals. Thereafter, in step 806, the surface area monitoring system will determine if the floor surface area was effectively cleaned. If the floor surface area was not effectively cleaned, the worker can receive an indication from the surface area monitoring system via, for example, a user output device on the floor cleaning device 710, a hard copy printout, an electronic display screen, an audible output, or a text message to a handheld device that the floor surface area is in need of additional cleaning in step 810. The worker will continue to clean the floor surface area and receive feedback iteratively until the surface area is determined to be clean in steps 806 and 810.

Figure 12:
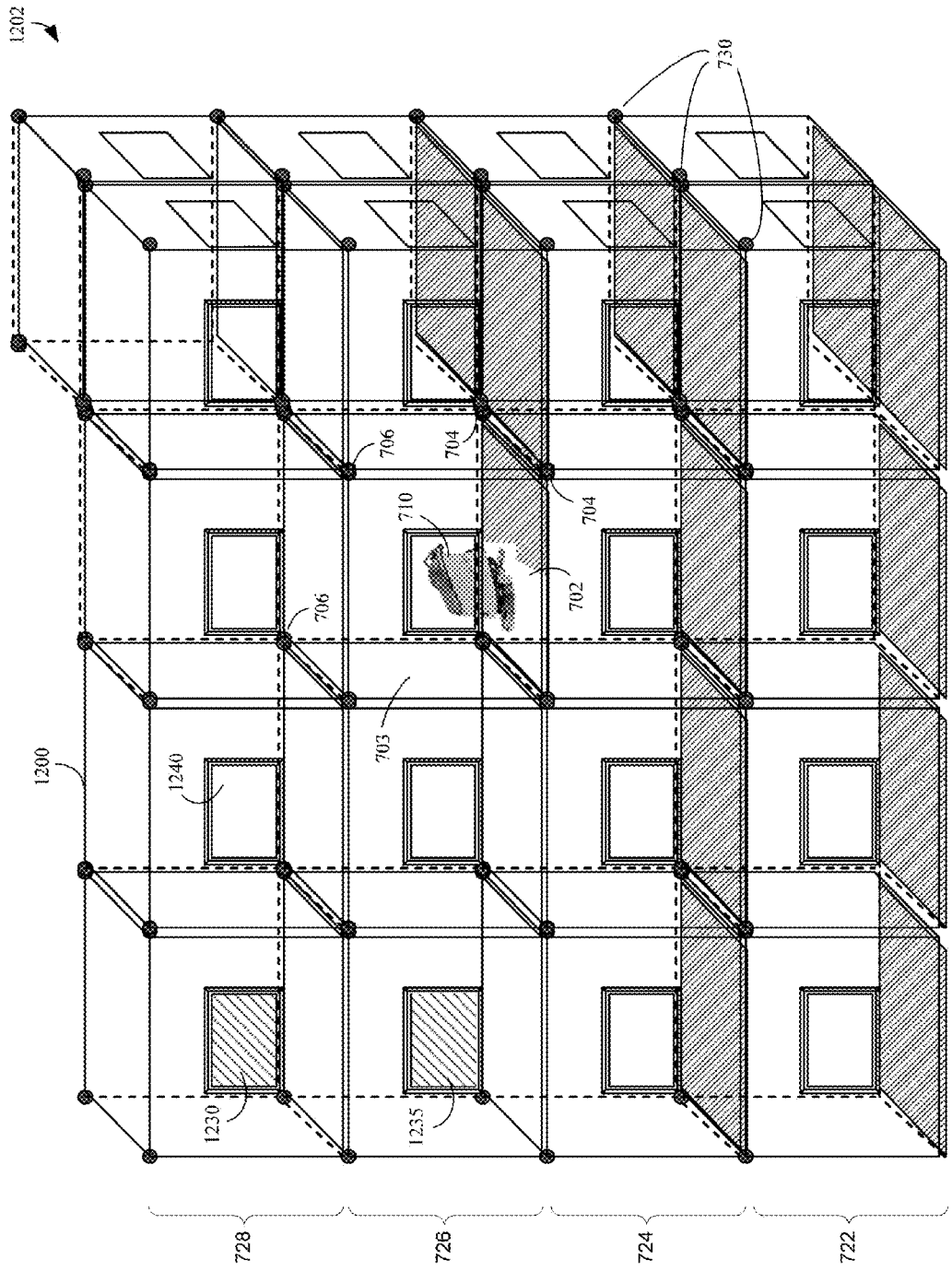
FIG. 12 shows a graphical display of an RTLS monitoring system.

In step 808, the surface area monitoring system may record data from the cleaning for long-term surface area cleaning analysis. The analysis can provide detailed feedback to the worker, supervisors, or auditors about cleaning habits. The analysis can allow suggestions for improvements to increase the effectiveness of cleaning, improve hygiene of the area monitored, and predict effectiveness of a particular cleaning regime. The method of FIG. 8 can be repeated to implement cleaning across multiple rooms, such as depicted in FIG. 12.

Figure 9:
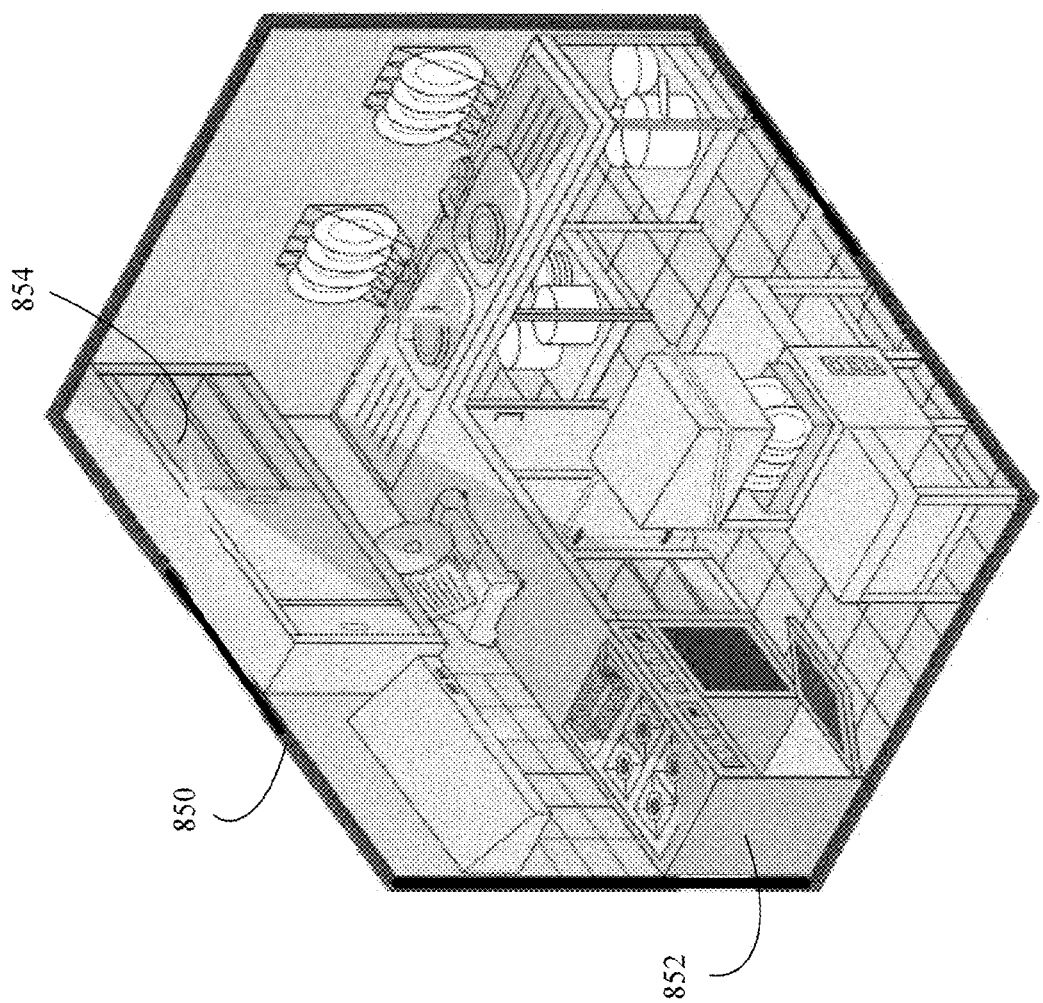
FIG. 9 shows a graphical display of RTLS used in 3-D surface cleaning monitoring.

A third implementation is a three-dimensional surface cleaning management and monitoring system using a RTLS (3D RTLS system) and will be described with reference to FIGS. 9-12. FIG. 9 shows a graphical layout 850 of a three-dimensional kitchen with multiple surfaces to be monitored. The 3D RTLS system uses the three-dimensional floor plan, which allows the system to manage and monitor the cleanliness of surfaces at different heights, sizes, and angles. Particular surfaces can be cleaned more efficiently with properly selected cleaning agents. Cleaning agents include all purpose cleaner/sanitizer, sanitizer, oven/grill cleaner, heavy duty degreaser, all purpose cleaner, stainless steel polish, among other types. For instance, surfaces inside an oven 852 are better cleaned using an oven or grill cleaning or heavy duty degreaser as opposed to an all purpose cleaner/sanitizer, which is more appropriate for use on shelves within cabinet 854. As with other embodiments of the RTLS system, the 3D RTLS system may visually illustrate the cleanliness of a surface using colors or shading on the graphical layout 850. In addition to illustrating the cleanliness of a surface, the 3D RTLS system is operable to visually illustrate a preferred cleaning agent for use with a particular surface. Moreover, the 3D RTLS system recommends the appropriate safety wear, such as goggles, gloves, masks, and the like, to be worn by an individual applying the preferred cleaning agent.

In one embodiment, a mobile cleaning cart includes a display screen. The display screen depicts the graphical layout 850. Each of the surfaces to be monitored is indicated as clean using, for instance, white coloring. If a surface is dirty, it has a non-white color that indicates both that the surface is dirty and the particular cleaning agent to be used. For instance, if the floor is depicted as blue, the floor is dirty and an all-purpose cleaner should be used. If a table top is pink, the table top is dirty and a stainless steel polish should be used. Other cleanliness and cleaning agent indicating techniques are contemplated for use within the 3D RTLS system.

FIGS. 10a-10d depict a simplified 3D graphical layout 900 of a kitchen for purposes of explanation. The graphical layout 900 includes a table 902 with a table top surface 904, which is a surface to be monitored. The 3D RTLS system also includes an active RFID enabled spray device 908 and active RFID enabled wipe device 910. The 3D RTLS system also includes fixed wireless access points 911 used to monitor the spray device 908 and wipe device 910. The spray device 908 and wipe device 910 are tracked automatically upon start-up or by manual enabling.

In the embodiments shown in FIGS. 10a-10d, the spray device 908 includes two RFID tags such that the 3D RTLS system is operable to determine the angle and direction of the spray device. Additional assumptions can be used to assist determining the angle and direction of a nozzle 912 of the spray device 908. For instance, the 3D RTLS system can assume that whenever the trigger is depressed, the spray device 908 is upright (i.e., the nozzle 912 is substantially above the base of the spray device). In other embodiments, additional RFID tags, accelerometers, and/or gravity-based directional sensors are used to assist in determining the angle and direction of the spray device 908.

Figure 10A:
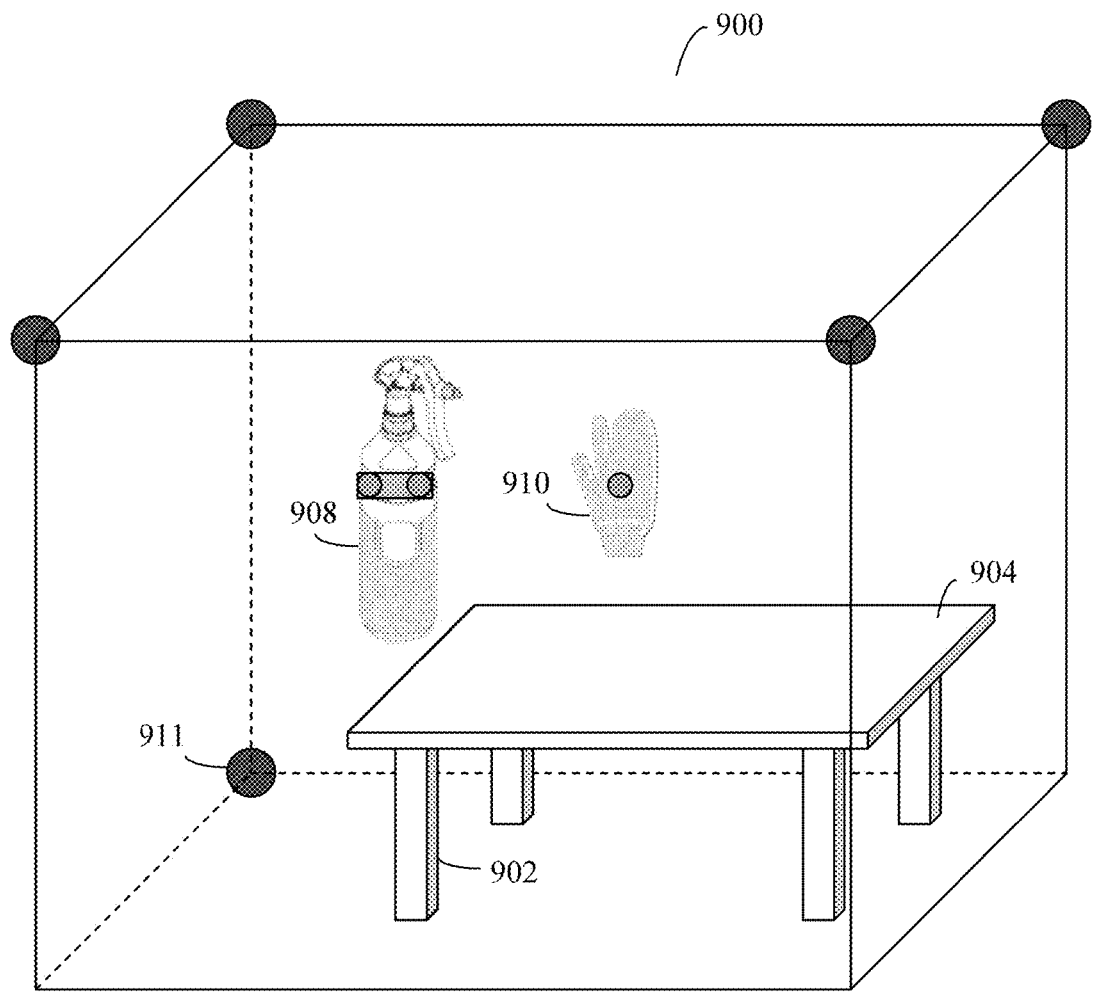
FIGS. 10a-d show a simplified graphical display of RTLS used in 3-D surface cleaning monitoring.
Figure 10B:
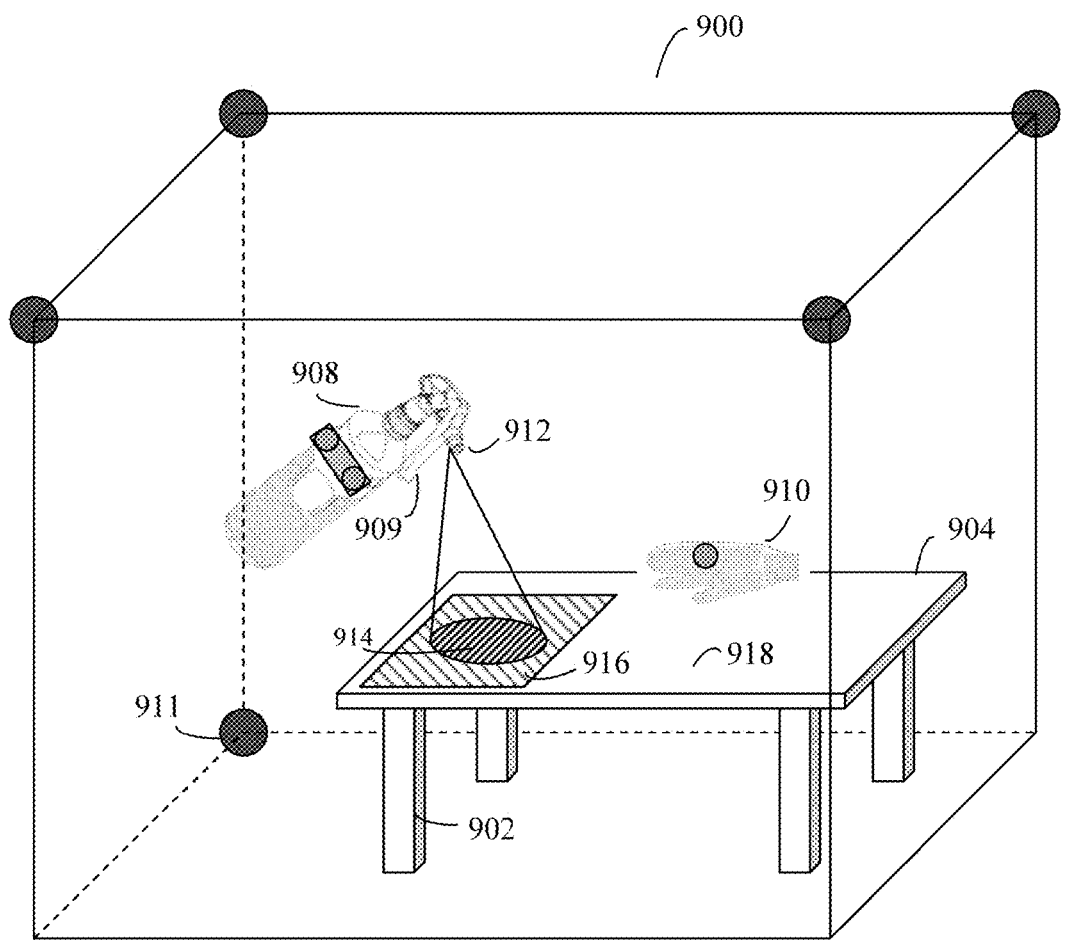
Figure 10C:
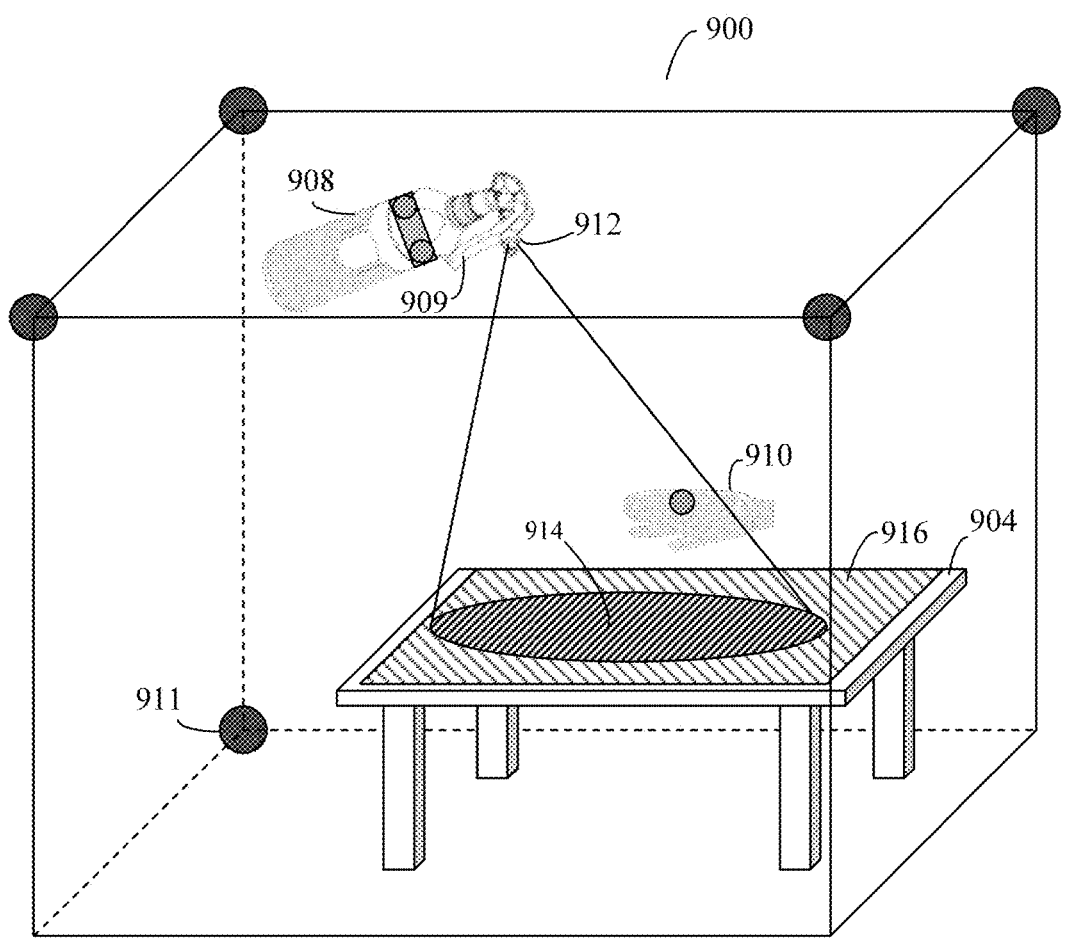

Turning to FIGS. 10b and 10c, the spray device 908 also wirelessly indicates to the management and monitoring system that the spray trigger 909 has been depressed (i.e., that a dispensement has occurred) and the level of depression. The 3D RTLS system uses the location of the nozzle 912 (determined using RTLS), along with the trigger depression signals from the spray device 908 to predict the spray pattern 914 on a surface. The predicted spray pattern 914 is predicted using the distance between the spray device 908 and a receiving surface such as table top surface 904, the level of depression of the spray trigger 909, and the location of nozzle 912. Generally, the nearer the spray device 908 is to the table top surface, the smaller the spray coverage area.

The 3D RTLS system then monitors the wipe device 910 to record and display the area of the table top surface that is wiped. The predicted spray pattern 914 and the area determined to be wiped by the wipe device 910 are used to estimate an effective wipe area 916 and areas where no chemical were applied 918. Known properties of the cleaning chemical, the table top surface 904, and the wipe device 910 can also be used to increase the accuracy of the estimated effective wipe area 916. For instance, some chemicals may have a larger potential coverage area than other chemicals. In addition, certain surfaces and wiping devices may be more conducive to larger effective wipe areas of chemicals.

FIG. 10b depicts a smaller spray pattern 914 than FIG. 10c, where the location of nozzle 912 is farther from the table top surface 904. Thus, since a majority of the top surface 904 remains uncleaned, the user should reapply the cleaning agent via the spray device 908 and wipe the area using wipe device 910. However, in FIG. 10c, the entire table except for a negligible area has been cleaned, and the 3D RTLS system will update the cleanliness indication by illustrating the table top surface as white.

The spray device 908 can also provide feedback via user output devices (not shown), such as indicator lights, a graphical display, or the like. The user output devices are affixed to the spray device 908, separate wireless devices, and/or separate wired devices. The 3D RTLS system employs the user output devices to inform the user of the cleanliness of the table top surface 904 before, during, and after the user has sprayed and wiped the table top surface 904 with a cleaning agent.

The user output devices can also be used to alert the user of surfaces in need of cleaning or of other pertinent information. In some embodiments, the user output devices are operable to indicate the type of cleaning agent to be used for a particular surface. For example, as the nozzle 912 is directed at or near a surface (as determined by the 3D RTLS system), a user output device on the spray device 908 indicates the type of cleaning agent to use and/or a type of wipe device 910. For instance, in FIG. 10d, the graphical layout 900 is divided into a first portion 919 and a second portion 920. The first portion 919 includes an oven/range 922 with range hood 924. The second portion 920 includes the table 902. When the 3D RTLS system determines that the spray device 908 and/or wipe device 910 are within the first portion 919, the system indicates via user output devices that an oven or grill cleaner or heavy duty degreaser should be used. In contrast, when the 3D RTLS system determines that the spray device 908 and/or wipe device 910 are within the second portion 920, the system indicates via user output devices that an all purpose cleaner/sanitizer should be used.

In some embodiments, the spray device 908 includes more than one type of cleaning agent therein and automatically selects the appropriate cleaning agent to dispense based on a proximate surface and the determined location of nozzle 912. If an improper or less effective cleaning agent is determined to have been used on a surface, the 3D RTLS system indicates as such using a user output device and indicates that the surface remains dirty or remains dirtier than if the proper cleaning agent was employed. In some embodiments, a user output device may include an alerting mechanism (e.g., an alarm or beep) to indicate when the spray device 908 has a cleaning agent that is incorrect or will harm a proximate surface. For example, a heavy duty degreaser may cause harm to the top surface 904 of the table 902.

Additionally, the 3D RTLS system is operable to notify a user to add attachments or make modifications to the spray device 908 and/or wipe device 910 based on the location of nozzle 912 and proximate surfaces. For instance, in some embodiments, the nozzle of the spray device 908 is automatically adjusted to change the spray pattern (e.g., narrower or wider) based on the location of nozzle 912 and proximate surfaces. For instance, if the location of nozzle 912 is near a surface, the nozzle may be adjusted to spray a wide pattern of cleaning agent to cover more surface area. However, as the nozzle is pulled away from the surface, the nozzle is adjusted to spray a narrower pattern to ensure that a ratio of cleaning agent to surface area is maintained above a threshold level.

Figure 10D:
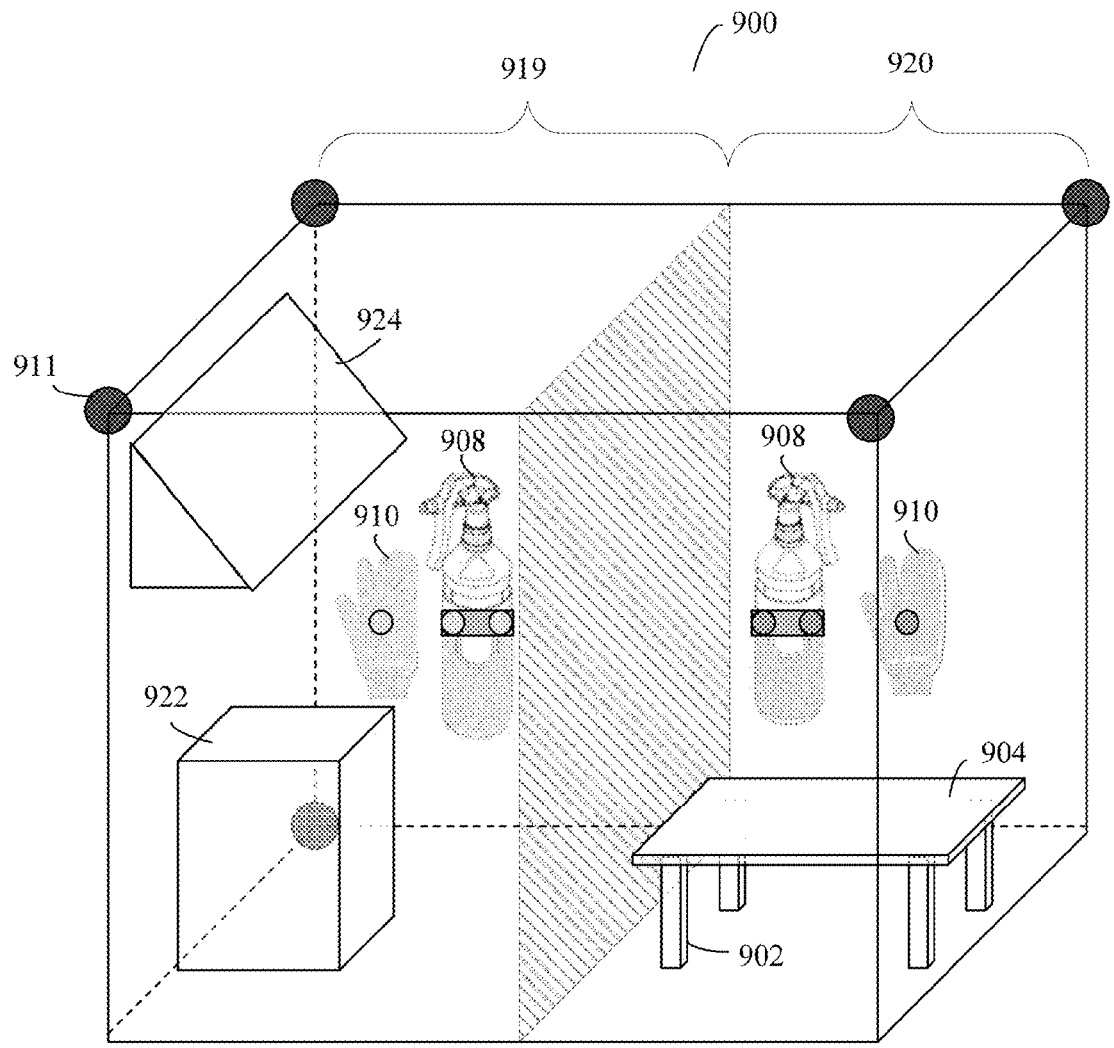
Figure 11:
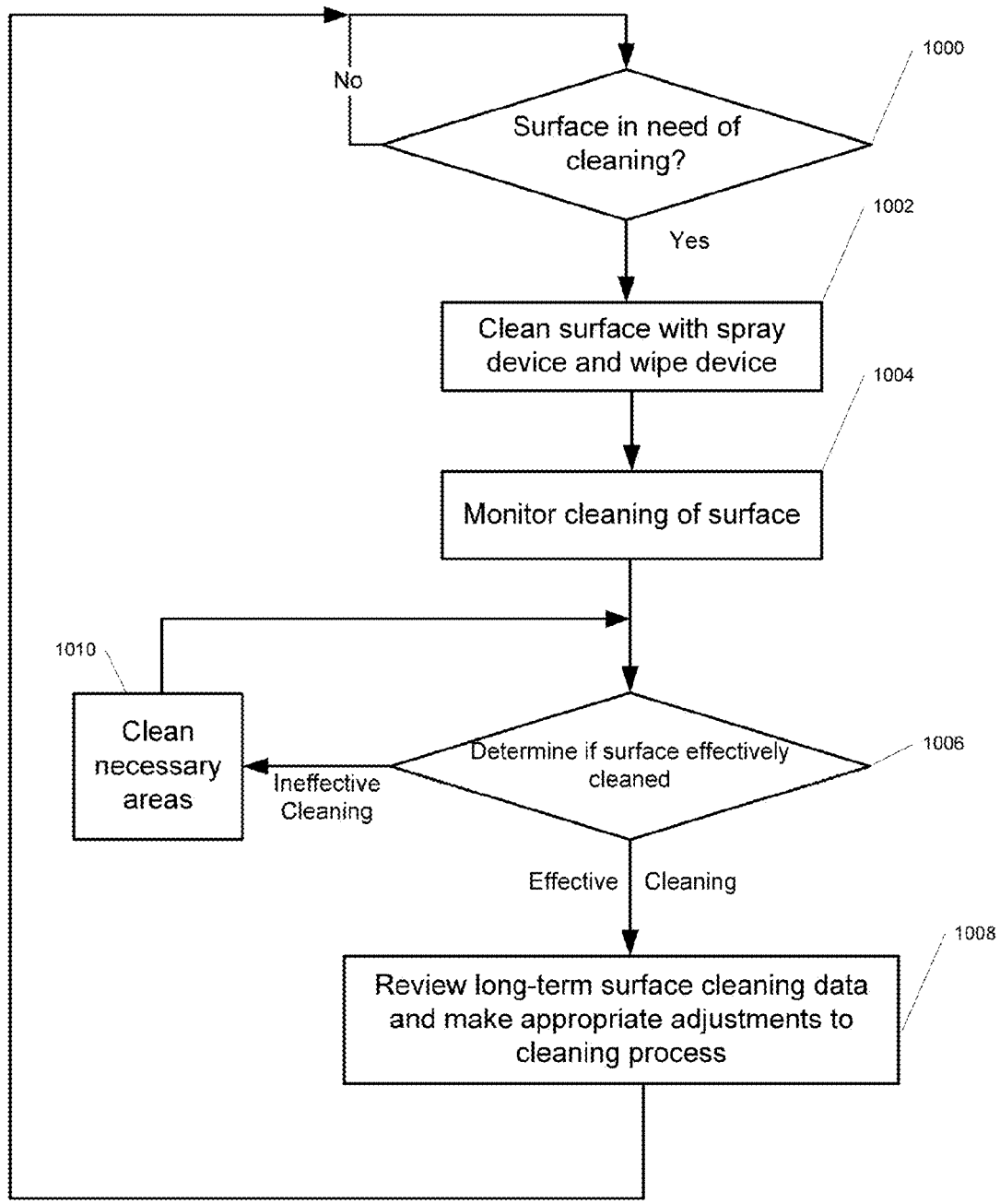
FIG. 11 shows a method of 3-D surface cleaning monitoring using RTLS.

FIG. 11 shows a flow chart for an exemplary method of operating the 3D RTLS system depicted in FIGS. 9-10d. In step 1000, a worker or the 3D RTLS system determines whether a surface area needs to be cleaned. If a surface area (such as table top surface 904) is determined to be in need of cleaning, a worker can be alerted by a user output device. In some embodiments, the 3D RTLS system recommends a cleaning agent and/or wipe device 910 for the surface area. In some embodiments, the RTLS system automatically selects a cleaning agent for the spray device 908 that includes multiple cleaning agents. In response, a worker will clean the surfaces with an active RFID spray device 908 and wipe device 910 in step 1002. In step 1004, the 3D RTLS system will monitor the cleaning of the surface area by predicting effective spray patterns and estimating effective wipe areas as described with respect to FIGS. 10a-10d. Thereafter, in step 1006, the 3D RTLS system will determine if the surface area was effectively cleaned. If the surface area was not effectively cleaned, the worker can receive an indication from the 3D RTLS system (e.g., via a user output device, a hard copy printout, or an electronic display screen), that the surface area is in need of additional cleaning in step 1010. The worker will continue to clean the surface area and receive feedback iteratively in steps 1006 and 1010 until the surface area is determined to be clean.

In step 1008, the 3D RTLS system may record data from the cleaning for long-term surface area cleaning analysis. The analysis can allow detailed feedback to the worker, supervisors, or auditors about cleaning habits. The analysis can allow suggestions for improvements to increase the effectiveness of cleaning, improve hygiene of the area monitored, and predict effectiveness of a particular cleaning regime. The method of FIG. 11 and the 3D RTLS system of FIG. 9, as well as other embodiments herein, may also be used for training and evaluating workers.

Each of the above implementations may be used alone or in conjunction with one another. For instance, in a combination system, the hygiene monitoring and management system can monitor room cleanliness based on traffic/use of the room, floor cleanliness from the surface area monitoring, and cleanliness of table top surfaces based on the 3D RTLS system. For example, if the floor or a table top surface is determined to be dirty based on traffic or use, the room will be marked dirty on the room cleanliness managing and monitoring system, and it will not be marked clean until the proper floor or table top surface cleaning has occurred. Other combinations are within the scope of the invention and would be apparent to one of ordinary skill in the art in light of this disclosure.

In the 3D RTLS system and method, the spray device 908 has at least two items monitored: the location of a dispenser port (e.g., the nozzle 912) and the actuation of a dispensing action (e.g., depressing spray trigger 909). The wipe device 910 is monitored to detect the spreading or application of a dispensed cleaning agent. Although the 3D RTLS system and method have been described for use with a particular type of spray device 908 with spray trigger 909 and wipe device 910, the application and use of 3D RTLS system and method are not limited to particular dispensing and wiping devices. Some embodiments of the invention incorporate other implements. In some embodiments, the spray device 908 includes a bottle with a flip-top cap that dispenses a cleaning agent using gravity and/or squeezing the bottle; an upright pelican pump dispenser that dispenses a cleaning agent when the pump is depressed; an automated dispensing device that receives an electrical signal to dispense and, in turn, dispenses a cleaning agent; or another dispensing device that dispenses a cleaning agent. In some embodiments, the wipe device 910 is a mop head, a sponge, a cloth, a mechanical scrubbing device, or another object used to spread or apply a dispensed cleaning agent. In some embodiments, the spray device 908 and wipe device 910 are combined into a single unit, for instance, a mop with an attached chemical dispenser.

FIG. 12 depicts a graphical layout 1200 of a facility 1202 that includes the floor cleaning device 710 in the room 703 depicted in FIG. 7. The facility 1202 includes four floors 1205, 1210, 1215, and 1220. In the embodiment depicted, most corners of each room include a wireless access point 1225. Using the labeling convention of FIG. 7, the level 1 access points 704 are positioned near the intersection of the second floor 1210 and the third floor 1215 and the level 2 access points 706 are positioned near the intersection of the third floor 1215 and the fourth floor 1220. Not all of the access points depicted in FIG. 7 are depicted in FIG. 12, and indeed, fewer or more access points are included in the facility 1202 of FIG. 12 in some embodiments.

Using RTLS as described above, the location and cleaning of the floor cleaning device 710 are tracked and plotted on the graphical layout 1200. For instance, the graphical layout 1200 depicts four floors of rooms, with each room having a cleanliness indication displayed. The rooms on the fourth floor 1220 are all determined to be clean and are indicated as such by not including shading. The rooms on the first floor 1205 and second floor 1210 are all determined to be dirty and are indicated as such using shading. Two rooms on the third floor 1215 are indicated as being clean, two rooms are indicated as being dirty, and one room (room 703) is in the process of being cleaned. In some embodiments, partial shading is used to display progress of on-going cleaning (see, e.g., room 703). In other embodiments, partial shading, color coding, or the like is used to depict levels of cleanliness, similar to graphical layout 500 of FIG. 5.

Although the high level graphical layout 1200 is displayed, a user is able to access a lower-level view. For example, the RTLS system displays the graphical layout 700 of FIG. 7 upon a user's selection of room 703. In some embodiments, a 3D graphical layout similar to those of FIGS. 9-10d is shown upon selection of an individual room. Additionally, the RTLS system displays a layout similar to graphical layout 500 of FIG. 5 upon a user's selection of a particular floor within the graphical layout 1200, such as the third floor 1215.

The surfaces to be monitored by the 3D RTLS system are not limited to horizontal surfaces. Rather, vertical surfaces (e.g., windows), surfaces on an angle (e.g., a range hood), and other surfaces are also monitored by the 3D RTLS system as described with reference to FIGS. 9 to 11. For instance, each room within the facility 1202 includes at least one window (e.g., windows 1230, 1235, and 1240). The windows 1230 and 1235 are dirty based on duration since a previous cleaning and/or other factors, and the graphical layout 1200 indicates that the windows 1230 and 1235 are dirty using shading. Similar to monitoring the table top surface 904, the 3D RTLS system monitors the windows' cleanliness levels by monitoring the spray device 908 and wipe device 910.

Various entities can use embodiments of the invention including, for example, managers of various settings (e.g., hospital management, office building management, etc.), government agencies (law enforcement agencies, environmental agencies, etc.), and consultants. These entities may use embodiments of the invention to both manage and monitor cleanliness and hygiene of an area, and also to train new and experienced personnel in effective cleaning techniques. Embodiments of the invention may be used in various settings, including, but not limited to, hospitals, schools, hotels, gyms, office buildings, homes, cruise ships, arenas, stadiums, or other areas where hygiene is valued. Embodiments of the invention can also be used to ensure complete or effective clean-up in scenarios where dangerous materials are present. For instance, government or other regulatory agencies may use embodiments of the invention to ensure effective asbestos removal, chemical spill clean-up, or other hazardous waste clean-up.

Additionally, although the disclosure has described systems using human cleaning personnel, it is within the scope of embodiments of the invention to use automated/robotic cleaning devices. Embodiments of the invention can direct one or more automated cleaning devices' cleaning and movement using the RTLS technology described above. For example, the floor cleaning device 710 can be an automated device that maneuvers and cleans without human interaction. A RTLS hygiene monitoring and management system as described above can be configured to select and dispatch the floor cleaning device 710 to tend to a particular room. Thereafter, the floor cleaning device 710 can be maneuvered using RTLS technology to clean the floor of that room.

In other embodiments, the wireless monitoring system is used for monitoring cleanliness of areas outside of a facility. For instance, a street RTLS system and method provides an improved method and system of coordinating general street cleaning and emergency snow removal. In the street RTLS system, wireless tags using a combination of wireless technologies (e.g., global positioning satellites, WiFi, ultrawide band, etc.) for triangulation are attached to street clearing devices including street cleaners, snow plows, brooms, and shovels. The street RTLS system includes a layout of the streets to be monitored (e.g., a digital road map) and tracks the street clearing devices. The street cleanliness levels are monitored using a combination of manual user input, passage of time, weather predictions, real-time weather input, precipitation sensors spaced out along the streets to be monitored, and other input means. The street RTLS system monitors the cleaning of streets and sidewalks by tracking the cleaning devices based on concepts described above with respect to FIGS. 1-12. Thus, a central operator of the street RTLS system is provided with a real-time cleanliness level of the streets that are monitored and directs street clearing devices accordingly.

In some embodiments, the RTLS systems described above are used to assist visually disabled or impaired persons. For instance, audible or Braille outputs work in conjuction with the RTLS systems in place of or in addition to the graphical outputs described above. Thus, a visually disabled or impaired person is operable to receive the benefits of the RTLS systems (e.g, receiving cleanliness level indications of surfaces and rooms).

Thus, the invention provides, among other things, a hygiene management and monitoring system and method that can provide beneficial graphical displays and interpretations of cleaning; information to better sustain, improve and audit a hygiene control system efficiently; and data for managing and controlling cleaning Additionally, a street monitoring method and system provides improved coordination of general street cleaning and emergency snow clearing.

The invention claimed is:

1. A method of hygiene monitoring and management comprising:
    transmitting wireless signals between a wireless tag and at least two access points;
    determining a distance between the wireless tag and each of the at least two access points;
    determining a location of the wireless tag with respect to the at least two access points based at least in part upon the distance between the wireless tag and each of the at least two access points;
    repeatedly determining the location of the wireless tag based on the tag distances to track movement of the wireless tag;
    determining a cleanliness level of an area based at least in part on tracking the movement of the wireless tag;
    graphically displaying
        a floor plan including the area,
            the determined cleanliness level of the area via a respective shading of at least three possible different shadings of the area, each of the shadings being associated with a corresponding cleanliness level, and
            at least one of a group including a current location of the wireless tag on the floor plan and a path indicating the tracked movement of the wireless tag on the floor plan.

2. The method of claim 1, wherein determining a location is based at least in part upon the strength of signals transmitted between the wireless tag and the at least two access points.

3. The method of claim 1, wherein the location of the wireless tag is performed by a locating module, the method further comprising moving the locating module with the tag.

4. The method of claim 1, wherein graphically displaying different cleanliness levels includes displaying different colors on the floor plan based at least in part upon the cleanliness level of the area.

5. The method of claim 1, wherein the floor plan and the cleanliness level are graphically displayed on a display, the method further comprising moving the display with the tag.

6. The method of claim 1, wherein transmitting wireless signals occurs between a wireless tag and at least three access points.

7. The method of claim 1, further comprising automatically changing dispense of chemicals in the area based at least in part upon the location of the wireless tag.

8. The method of claim 1, further comprising notifying a user of a cleaning action to take when the wireless tag reaches a predetermined location relative to the access points.

9. The method of claim 1, wherein determining the cleanliness level is based in part upon at least one of a group selected of a fixed call actuator output, a total duration of the wireless tag being present in the area, and a total quantity of trips into the area by the wireless tag.

10. The method of claim 1, wherein the area comprises a floor surface.

11. A hygiene monitoring and management system comprising:
    a wireless tag;
    at least two access points operable to communicate wirelessly with the wireless tag;
    a locating module operable to
        repeatedly determine a location of the wireless tag; and
        track movement of the wireless tag based at least in part upon repeated determinations of location of the wireless tag;
    a management module operable to receive data regarding the tracked movement of the wireless tag, and to generate a graphical representation of a cleanliness level of an area determined based at least in part upon the tracked movement,
    wherein the graphical representation of the determined cleanliness level is defined by a respective displayed shading of at least three possible different shadings of the area, and wherein each of the shadings is associated with a corresponding cleanliness level.

12. The hygiene monitoring and management system of claim 11, wherein the locating module determines the location of the wireless tag based at least in part upon the strength of signals transmitted between the wireless tag and the at least two access points.

13. The hygiene monitoring and management system of claim 11, wherein the locating module moves with the wireless tag.

14. The hygiene monitoring and management system of claim 11, wherein the graphical representation of the different cleanliness levels comprises different colors corresponding to the cleanliness level of the area.

15. The hygiene monitoring and management system of claim 11, further comprising a display upon which the graphical representation is displayed, wherein the display is movable with the tag.

16. The hygiene monitoring and management system of claim 11, wherein the locating module repeatedly determines the location of the wireless tag with three access points.

17. The hygiene monitoring and management system of claim 11, wherein the management module also automatically changes dispense of chemicals in the area based at least in part upon the location of the wireless tag.

18. The hygiene monitoring and management system of claim 11, wherein the management module generates a notification to a user of a cleaning action to take when the wireless tag reaches a predetermined location relative to the access points.

19. The hygiene monitoring and management system of claim 11, wherein the management module is also adapted to determine the cleanliness level based at least in part upon at least one of a group selected of a fixed call actuator output, a total duration of the wireless tag being present in the area, and a total quantity of trips into the area by the wireless tag.

20. The hygiene monitoring and management system of claim 11, wherein the area comprises a floor surface.

21. A method of hygiene monitoring and management comprising:
    transmitting wireless signals between a wireless tag and at least two access points;
    determining a distance between the wireless tag and each of the at least two access points;
    determining a location of the wireless tag with respect to the at least two access points based at least in part upon the distance between the wireless tag and each of the at least two access points;
    repeatedly determining the location of the wireless tag based at least in part on the tag distances to track movement of the wireless tag;
    determining a cleanliness level of an area based at least in part on tracking the movement of the wireless tag;
    graphically displaying
        a floor plan with a plurality of areas-including the area,
        different cleanliness levels of at least three of the plurality of areas via different shadings of each area for which the cleanliness levels are displayed, each of the shadings being associated with a corresponding cleanliness level, and
        at least one of a group including a current location of the wireless tag on the floor plan and a path indicating the tracked movement of the wireless tag on the floor plan.

* * * * *